(12) United States Patent
Bour et al.

(10) Patent No.: US 7,569,019 B2
(45) Date of Patent: Aug. 4, 2009

(54) ANALYSIS AND USE OF CARDIOGRAPHIC BIOIMPEDANCE MEASUREMENTS

(76) Inventors: Frank Bour, 44, rue de Laborde, 75008 Paris (FR); Jean Joseph Bour, 21, rue de Stade, 57730 Petit-Ebersviller (FR)

( * ) Notice: Subject to any disclaimer, the term of this patent is extended or adjusted under 35 U.S.C. 154(b) by 600 days.

(21) Appl. No.: 11/454,248

(22) Filed: Jun. 16, 2006

(65) Prior Publication Data

US 2007/0293770 A1 Dec. 20, 2007

(51) Int. Cl.
*A61B 5/0295* (2006.01)
(52) U.S. Cl. ............... 600/526; 600/508; 600/513; 607/2; 607/27
(58) Field of Classification Search ........... 600/526
See application file for complete search history.

(56) References Cited

U.S. PATENT DOCUMENTS

| | | | | |
|---|---|---|---|---|
| 4,535,774 | A * | 8/1985 | Olson | 607/24 |
| 4,733,667 | A * | 3/1988 | Olive et al. | 607/24 |
| 4,807,638 | A * | 2/1989 | Sramek | 600/485 |
| 5,423,326 | A * | 6/1995 | Wang et al. | 600/526 |
| 6,161,038 | A | 12/2000 | Schookin et al. | |
| 2005/0203427 | A1 * | 9/2005 | Judy | 600/506 |
| 2007/0005114 | A1 * | 1/2007 | Salo et al. | 607/17 |
| 2007/0066905 | A1 * | 3/2007 | Zhang | 600/509 |

FOREIGN PATENT DOCUMENTS

EP 1304074 4/2003

OTHER PUBLICATIONS

Braun et al., "Impedance Cardiography as a Noninvasive Technique for Atrioventricular Interval Optimization in Cardiac Resynchronization Therapy", Journal of Interventional Cardiac Electrophysiology, Kluwer Academic Publishers, vol. 13, No. 3, Sep. 1, 2005, pp. 223-229.
Gimbel et al., "Method and Demonstration of Direct Confirmation of Response to Cardiac Resynchronization Therapy Via Preimplant Temporary Biventricular Pacing and Impedance Cardiography", American Journal of Cardiology, Cahners Publishing Co., Newton, MA, USA, vol. 96, No. 6, Sep. 15, 2005, pp. 874-876.

* cited by examiner

*Primary Examiner*—Kennedy J Schaetzle
(74) *Attorney, Agent, or Firm*—Fish & Richardson P.C.

(57) ABSTRACT

A technique for analyzing cardiographic measurements includes receiving bioimpedance information of a subject and determining a rate of change of blood flow based on the bioimpedance information. If the rate of change of blood flow includes at least two peaks during the systole of the subject, a time difference based on at least one of the two of the peaks is determined and compared to a threshold time. A technique for using the cardiographic measurements of the subject further includes if the determined time is greater than the threshold time, implanting a pacemaker in the subject and if the determined time is not greater than the threshold time, not implanting a pacemaker in the subject.

18 Claims, 11 Drawing Sheets

If the LV Outflow Onset is Occuring between the RV Onset Flow and 0 RV DZ' : Dome Shaped DZ'

LV Outflow Onset Starts after the RV Outflow Onset

The Max LV DZ' is Clearly after the Max RV DZ'

The Cumulative Max DZ' is Over the Middle of Max RV DZ' and Max LV DZ'

S' is the Nadir between S1 and Max LV DZ' (S2)

⟷ = LV Outflow Onset - RV Outflow Onset = S1 S'

S1-S' is the Phase Delay

DZ' is Notched with a W Shape

LV Outflow Onset begins after the Max RV DZ'

ANALYSIS AND USE OF CARDIOGRAPHIC BIOIMPEDANCE MEASUREMENTS

TECHNICAL FIELD

The subject matter described herein relates to analyzing and using cardiographic measurements and more particularly, to analyzing and using cardiographic measurements to detect interventricular and intraventricular asynchronism.

BACKGROUND

Cardiologists have a variety of tools available for diagnosing and treating heart conditions. For example, cardiologists may use electrocardiograms (ECGs), echocardiograms, and magnet resonance imaging (MRI) to diagnose and assist in the treatment of heart conditions. Each of these techniques uses different technologies to generate different measurements and/or indications of the condition and operation of the heart. Also, each of these techniques has advantages and disadvantages.

An echocardiogram is an ultrasound-based assessment of the heart. In echocardiograms, ultrasound techniques are used to produce two-dimensional slices and three-dimensional images of the heart. Echocardiograms may be invasive or non-invasive. In a non-invasive echocardiogram, the echocardiography transducer (or probe) may be placed on the chest wall (or thorax) of the subject, while images are taken through the chest wall. This non-invasive technique provides an accurate and quick assessment of the overall health of the heart. With this information, a cardiologist can quickly assess a patient's heart valves and degree of heart muscle contraction (using the ejection fraction). In an invasive echocardiogram, a specialized scope containing an echocardiography transducer (TEE probe) may be inserted into the patient's esophagus, while images are taken from there. In addition to creating images of the cardiovascular system, the echocardiogram can also produce measurements of the velocity of blood and cardiac tissue at arbitrary points using pulsed or continuous wave Doppler ultrasound. Echocardiograms are typically expensive, are difficult to administer and read, and require a trained technician to perform the echocardiogram.

An MRI uses magnetic fields to produce accurate images of internal body parts such as the heart. As with echocardiograms, a cardiologist may use an MRI to quickly assess a patient's heart valves and degree of heart muscle contraction. MRI's, however are very expensive. Further, people who have a pacemaker or an implantable cardioverter defibrillator implanted in their body typically are not allowed to have an MRI.

Impedance cardiography (ICG) is a technology that measures thoracic impedance changes, which are related to changes in blood volume in the heart. As such, ICG may be used to used to track volumetric changes in blood flow during the cardiac cycle. In ICG, probes are non-invasively placed near the patient's ribs and neck and an alternating current is transmitted through the patient's chest via the probes. As blood volume and velocity in the heart change within each heart cycle, the ICG measures changes in impedance and calculates a corresponding blood volume and velocity. As such, ICG may be used to measure stroke volume, cardiac output, systemic vascular resistance, velocity index, acceleration index, thoracic fluid content, systolic time ratio, left ventricular ejection time, pre-ejection period, left cardiac work, heart rate, and the like.

An ECG measures electrical potential between various points of the body. The ECG produces a familiar chart of electrical activity with time, as shown in FIG. 1, that represents the electrical activity of the heart. The ECG is non-invasive and relatively inexpensive.

As shown in FIG. 1, the ECG 100 includes a P wave, a PR segment, a QRS complex, and ST segment, and a T wave. The P wave is the electrical signature of the current that causes atrial contraction (both the left and right atria typically contract generally simultaneously). The PR segment connects the P wave and the QRS complex. The QRS complex (including a Q wave, an R wave, and an S wave) corresponds to the current that causes contraction of the left and right ventricles, which is typically much more forceful than that of the atria and involves more muscle mass, thus resulting in a greater ECG deflection, as shown. The Q wave, when present, represents the small horizontal (left to right) current as the action potential travels through the interventricular septum. The R and S waves indicate contraction of the myocardium. The ST segment connects the QRS complex and the T wave. The T wave represents the repolarization of the ventricles.

The PR interval is measured from the beginning of the P wave to the beginning of the QRS complex. The PR interval is usually 0.12 to 0.20 seconds. The duration of the QRS complex is normally less than or equal to 0.10 second. The QT interval is measured from the beginning of the QRS complex to the end of the T wave. A normal QT interval is usually about 0.40 seconds.

Because the ECG provides information about the electrical activity of the heart, ECGs are often used in diagnosing and treating heart patients. Many rules of thumb have been developed for diagnosis based on ECGs. For example, a P wave rate less than 60 may indicate sinus bradycardia while a P wave rate greater than 100 may indicate sinus tachycardia. A PR interval longer than 0.20 seconds may indicate first-degree heart blockage.

As can be seen, there are great deal of cardiographic measurements that can be used in diagnosing and treating heart conditions. One particular heart condition is called interventricular asynchronism which is a condition in which the timing between the contractions of the different chambers of the heart is out of synch, resulting is suboptimal cardio performance. Another condition is called intraventricular asynchronism which is a condition in which the timing of the contractions within a single chamber of the heart is out of synch, resulting in suboptimal cardio performance. Interventricular and intraventricular asynchronism can often be treated with a pacemaker while many other heart conditions do not respond to a pacemaker.

One technique for diagnosing asynchronism relies on measurements from an ECG, specifically, the QRS complex. A QRS complex width of greater than 0.12 seconds duration, associated with an echographic ejection fraction below 35%, has been used to predict the existence of asynchronism. Many patients with a QRS complex width of greater than 0.12 seconds are eventually treated with a pacemaker. Many of these pacemaker patients (about 30%), however, do not actually have asynchronism and thus do not get improvements from the pacemaker. On the other hand, some patients with a QRS complex width less than a 0.12 second duration do suffer from asynchronism and would nonetheless not be implanted with a pacemaker under conventional techniques, and thus a therapeutic benefit is missed. Further, many patients having asynchronism and a pacemaker receive only marginal improvements from the pacemaker. Therefore, there is a need for better techniques for identifying patients who are more likely to respond to a pacemaker and for identifying patients who are likely to benefit from pacemaker adjustment.

SUMMARY

A technique for analyzing cardiographic measurements includes receiving bioimpedance information of a subject; determining a rate of change of blood flow based on the bioimpedance information; determining if the rate of change of blood flow includes at least two peaks during the systole of the subject; if the rate of change of blood flow includes at least two peaks, determine a time difference based on at least one of the two peaks; and compare the determined time to a threshold time.

A technique for using cardiographic measurements of a subject includes determining a rate of change of blood flow; determining if the rate of change of blood flow has at least two peaks during the systole of the subject; if there are at least two peaks, determine a time difference based on at least one of the two peaks; compare the determined time to a threshold time; if the determined time is greater than the threshold time, implanting a pacemaker in the subject; and if the determined time is not greater than the threshold time, not implanting a pacemaker in the subject. Further, adjustments may be made to the pacemaker (including, for example stimulation delay adjustments, probe position adjustments, and the like) based on the cardiographic measurements, for example, the time difference between the two peaks.

Computer program products, tangibly embodied in information carriers are also described. Such computer program products may cause a data processing apparatus to conduct one or more operations described herein.

Similarly, systems are also described that may include a processor and a memory coupled to the processor. The memory may encode one or more programs that cause the processor to perform one or more of the operations described herein.

The details of one or more variations of the subject matter described herein are set forth in the accompanying drawings and the description below. Other features of the subject matter described herein will be apparent from the description and drawings, and from the claims.

DESCRIPTION OF DRAWINGS

Like reference symbols in the various drawings indicate like elements.

DETAILED DESCRIPTION

As described above, impedance cardiography (ICG) measures thoracic impedance which is related to blood volume in the aorta. ICG may be used to determine stroke volume, cardiac output, systemic vascular resistance, velocity index, acceleration index, thoracic fluid content, systolic time ratio, left ventricular ejection time, pre-ejection period, heart rate, and the like. Further, ICG measurements may be combined with ECG measurements and blood pressure measuring devices to obtain additional information (e.g., systemic vascular resistance and left cardiac work).

There are multiple parameters of the heart cycle that may be determined and/or estimated based on ECG and ICG Stroke volume (SV) is the amount of blood the left ventricle ejects in one beat and may be measured in milliliters per beat (ml/beat). Cardiac Output (CO) is the amount of blood the left ventricle ejects into the systemic circulation in one minute, measured in liters per minute (l/min). CO can be determined by multiplying SV by Heart Rate (HR). Systemic Vascular Resistance (SVR) represents the force that the left heart must pump against in order to deliver the stroke volume into the periphery.

SVR is directly proportional to blood pressure and indirectly proportional to blood flow (CO). Velocity Index (VI) is the maximum rate of impedance change and is representative of aortic blood velocity. Acceleration Index (ACI) is the maximum rate of change of blood velocity and is representative of aortic blood acceleration. Thoracic Fluid Content (TFC) is representative of total fluid volume in the chest, including both intra-vascular and extra-vascular fluid. TFC may be calculated as the inverse of the baseline impedance measurement. Baseline impedance is directly proportional to the amount of conductive material (e.g., blood, lung water) in the chest.

Pre-Ejection Period (PEP) is the measured interval from the onset of ventricular depolarization (Q-wave in an ECG) to the beginning of mechanical contraction (first upslope of the impedance waveform). Left Ventricular Ejection Time (LVET) is the time from aortic valve opening to aortic valve closing. Systolic Time Ratio (STR) is inversely proportional to left ventricular function, and may be calculated as the Pre-Ejection Period (PEP) divided by the Left Ventricular Ejection Time (LVET). Left Cardiac Work (LCW) parallels myocardial oxygen consumption, and is related to the product of blood pressure and blood flow. Heart Rate (HR) is the number of heartbeats per minute, which can be measured from the ECG.

Figure 1:
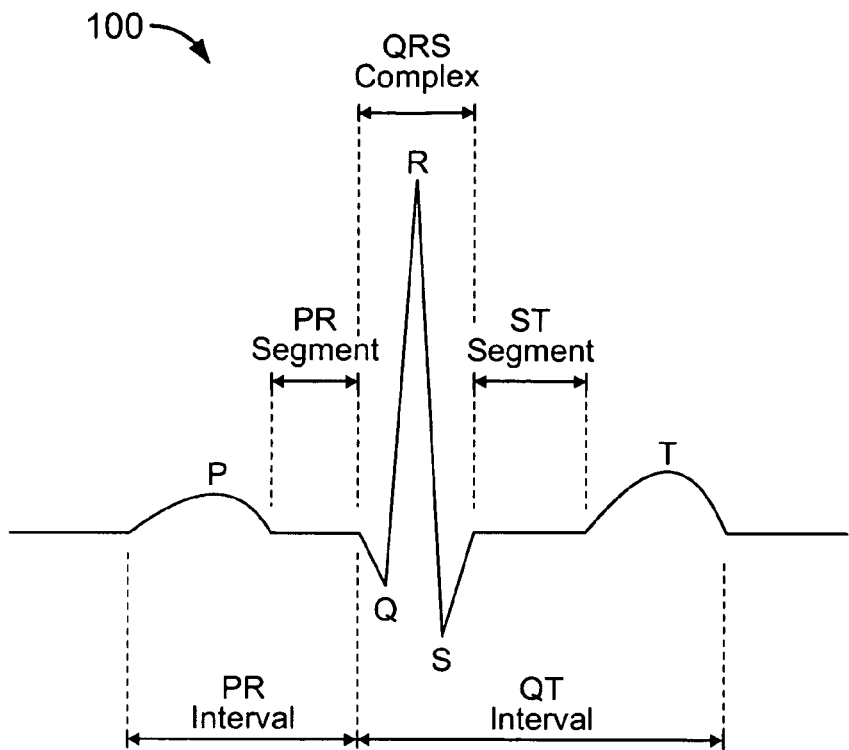
FIG. 1 is a diagram of an exemplary electrocardiogram.
Figure 2:
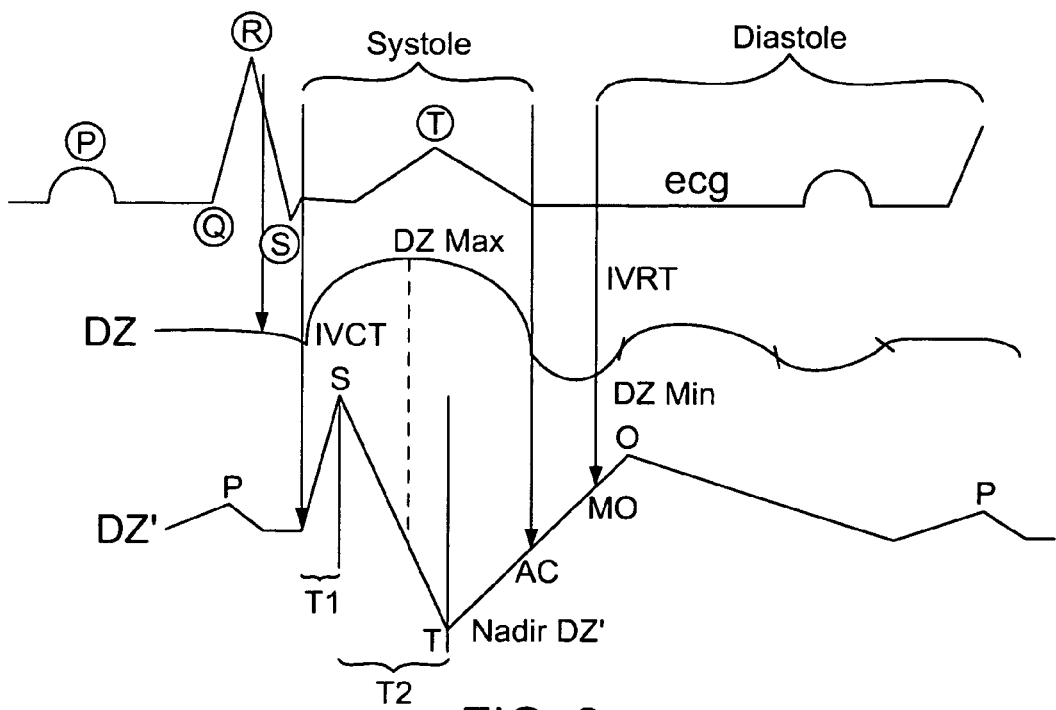
FIG. 2 shows an illustrative electrocardiograms (ECG) signal, an illustrative impedance cardiography (ICG) signal DZ representative of normal blood flow through the heart, and an illustrate ICG signal DZ' representative of the acceleration or mathematical first derivate of the signal DZ.

In addition to determining such cardiovascular measures, ICG may also provide a continuous representation of blood flow through the heart. FIG. 2 shows an illustrative ECG signal, an illustrative ICG signal DZ representative of normal blood flow through the heart, and an illustrate ICG signal DZ' representative of the acceleration or mathematical first derivate of the signal DZ, all plotted with time. The ECG signal is similar to that described in connection with FIG. 1.

The signal DZ includes a first portion during the systole that begins at about the isovolumic contraction time (IVCT) and ends at about when the aortic valve closes (AC). The signal DZ includes a second portion during the diastole that begins about when the mitral valve opens (MO) (and the isovolumic relaxation time) and ends about the time of the QRS complex of the ECG signal. The signal DZ includes a peak DZ max (in the first portion of the signal DZ) and a nadir DZ min (in the second portion of the signal DZ). The nadir (low part) of the curve corresponds to the opening of the mitral valve (MO).

The signal DZ' includes a first potion having a small peak P, a second portion having a larger peak S, a third portion having a nadir T, and a fourth portion having a small peak O. Peak P of signal DZ' occurs subsequently and shortly after the P wave of the ECG signal. Peak S of signal DZ' occurs subsequently and shortly after the QRS complex of the ECG signal. Nadir T of signal DZ' occurs around the time of the T wave of the ECG signal. Peak O of signal DZ' occurs subsequently and shortly after the T wave of the ECG signal. Time T1 is the time that signal DZ' increases to peak S and time T2 is the time that signal DZ' decreases from peak S to nadir T.

Normally, electric activation of the heart starts after the ECG Q point of the QRS complex. The mitral and tricuspid leaflets typically close around the ⅓ and ⅔ junction points of the descending part of the R wave of the ECG as both right and left intra ventricular pressure becomes higher than the atrial pressure. Even if electric activation occurs simultaneously in the two contractile chambers, the pulmonary valve may open about nearly 10 milliseconds before the aortic valve due to different pressures in the two great cardiac arteries. The right ventricle isovolumic contraction time (IVCT) ends with the onset of pulmonic flow onset when the intraventricular pressure rises over about 15 mmHg, whereas the aortic cusps are spreading when the left ventricular passes the diastolic blood pressure. Under a delay between both blood ejections of 24 milliseconds, the mean cumulative curves of the signal DZ and the signal DZ' are overlapping resulting in a smooth dome visible during their maximum value. Intra-cardiac volume modifications are electrically related to the signal DZ which is the cumulative representation of right and left ventricle haemodynamical activity.

Figure 3:
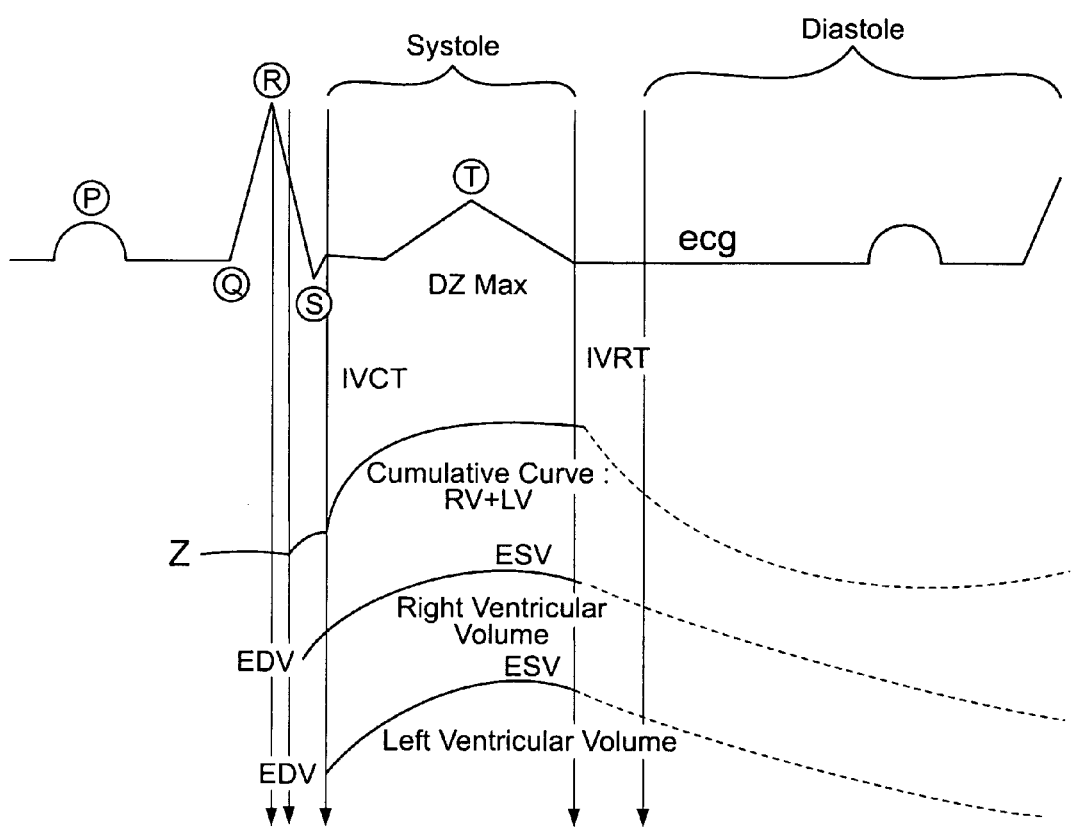
FIG. 3 shows the ECG signal of FIG. 2 plotted with an ICG signal Z that represents the total volume of blood in the both the right and left ventricles.

FIG. 3 shows the ECG signal of FIG. 2 plotted with an ICG signal Z that represents the total volume of blood in the both the right and left ventricles. As can be seen, the signal Z includes a first portion (of short duration) that increases over time and a second portion (of longer duration) that increases more quickly over time. Signal Z also includes a third portion of decreasing volume representing the emptying of the ventricles. Signal Z can be divided into its constituent parts, including both the right ventricular volume and the left ventricular volume. As can be seen, the right ventricular volume begins increasing slightly earlier (e.g., a few milliseconds) than the left ventricular volume, resulting in signal Z having two portions each with a different amount of increase.

Figure 4:
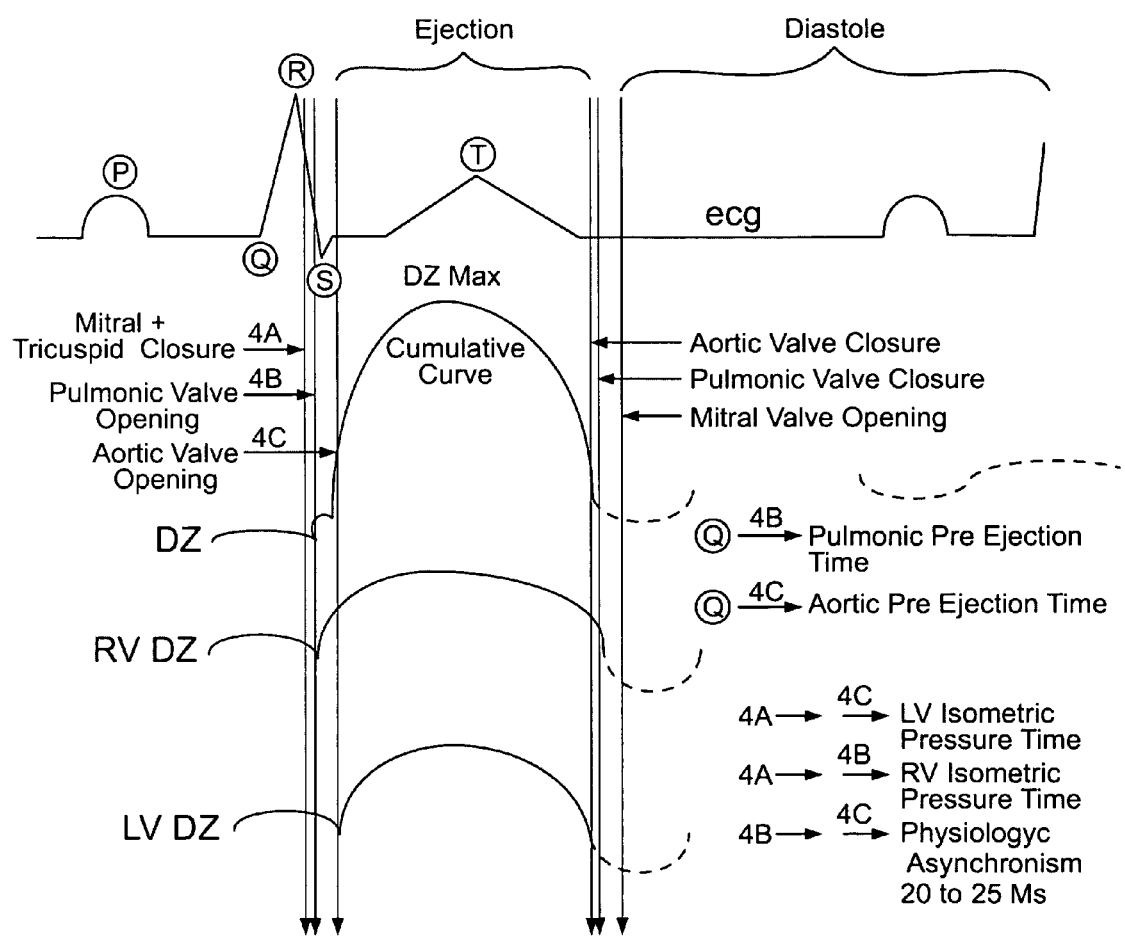
FIG. 4 shows the ECG signal of FIG. 2 plotted with an ICG signal DZ, the signal RV DZ representative of the flow through the right ventricle (and a component of the signal DZ), and the signal LV DZ representative of the flow through the left ventricle (another component of the signal DZ).

FIG. 4 shows the ECG signal of FIG. 2 plotted with an ICG signal DZ, the signal RV DZ representative of the flow through the right ventricle (and a component of the signal DZ), and the signal LV DZ representative of the flow through the left ventricle (another component of the signal DZ). As can be seen, in similar fashion as FIG. 3, the right ventricular flow begins increasing slightly earlier (e.g., a few milliseconds) than the left ventricular flow, resulting in signal DZ having two portions each with a different amount of increase. The superposition and addition of the two nearly overlapping component curves (signal RV DZ and signal LV DZ) creates a smooth cumulative signal DZ, which is representative of the whole intra-cardiac fluid flow.

Figure 5:
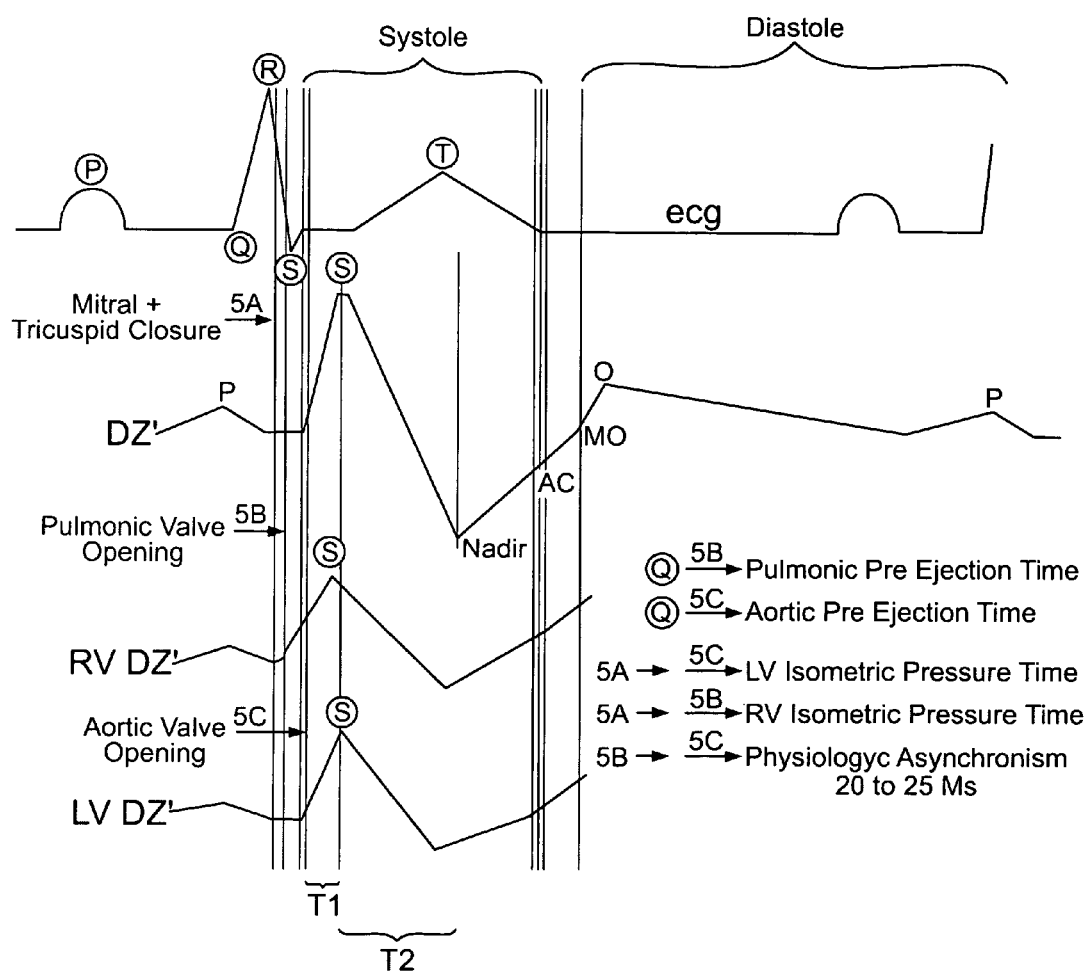
FIG. 5 shows the ECG signal of FIG. 2 and the ICG signal DZ' of FIG. 2 plotted with the signal RV DZ' representative of the acceleration of the flow through the right ventricle (and a component of the signal DZ'), and the signal LV DZ' representative of the acceleration of the flow through the left ventricle (another component of the signal DZ').

FIG. 5 shows the ECG signal of FIG. 2 and the ICG signal DZ' of FIG. 2 plotted with the signal RV DZ' representative of the acceleration of the flow through the right ventricle (and a component of the signal DZ'), and the signal LV DZ' representative of the acceleration of the flow through the left ventricle (another component of the signal DZ'). As can be seen, the RV DZ' signal and the LV DZ' signal are similar in shape but begin at slightly different times. If the RV DZ' signal and the LV DZ' signal begin at significantly different times, then the patient may have interventricular asynchronism.

The maximum value of DZ' is referred to as DZ' max. Time T1 (which is the time difference between the onset of DZ' and DZ' max) is referred to as the positive part of the systolic contraction, whereas time T2 (which is the time from DZ' max to the DZ' min) is referred to as the negative part of the systolic contraction. If T1/T2 is low, the patient may be prone to fainting. DZ' min is not the end of the systolic ejection, but the contractility inflection point. The end of the ascending part of the signal DZ' is not a positive acceleration but the inversion moment of the negative contractility, preparing the closing of the aortic leaflets just before the isovolumetric relaxation which is followed by the mitral opening.

The time from the Q wave of the ECG signal to the onset of the signal DZ' is the pre-ejection time. The isovolumetric contraction time is calculated from the closing of the atrial leaflets to the onset of the signal DZ'. The systole is the sum of these two time intervals and the effective ejection period.

Rather than attempt to determine the difference in beginning times of the individual valve contractions, however, such phase difference between the two ventricles may be observed using the peak S of the DZ' signal, as described in more detail in connection with FIG. 6.

Figure 6:
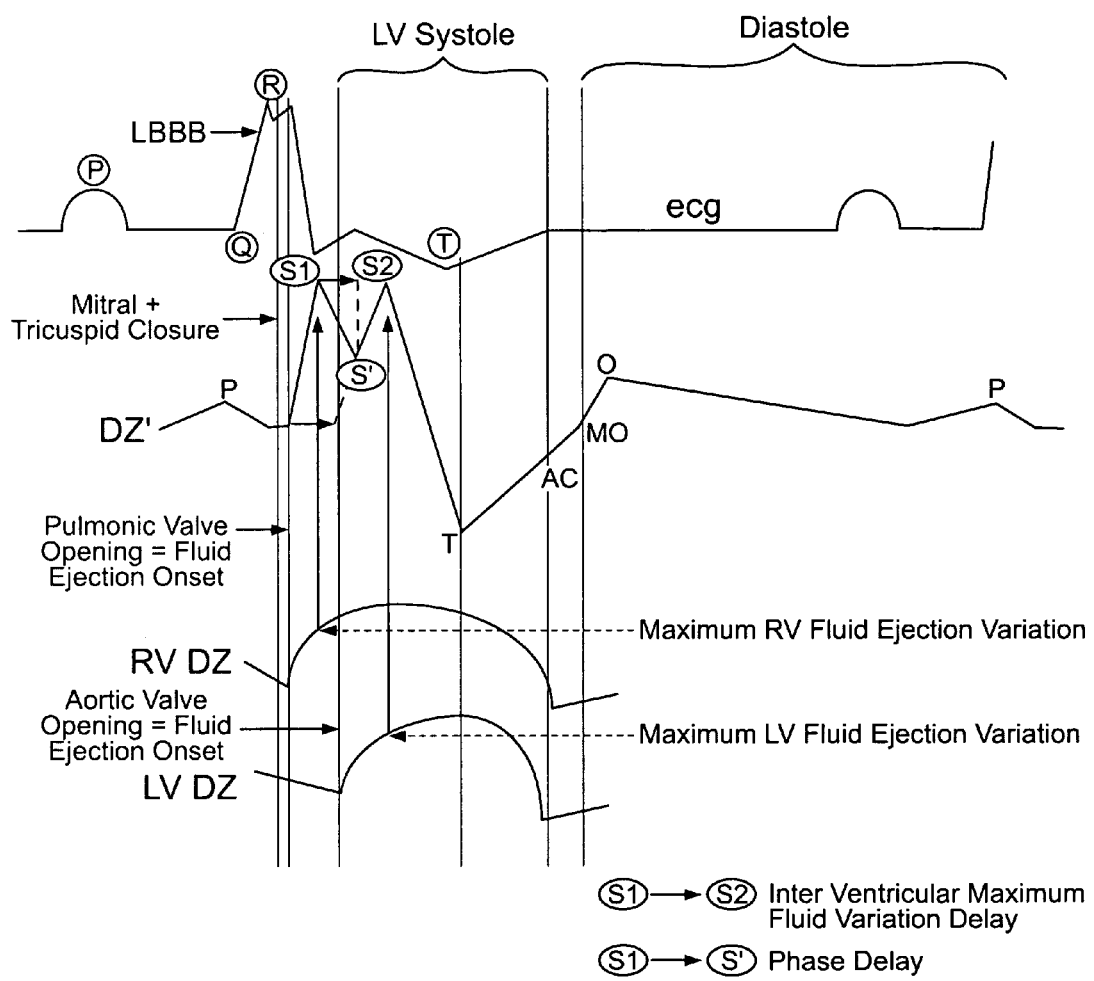
FIG. 6 shows an ECG signal similar to that of FIG. 2 (except for a patient with asynchronism), an ICG signal DZ' similar to that of FIG. 2 (except for a patient with asynchronism), a signal RV DZ representative of the flow through the right ventricle (and a component of the signal DZ), and a signal LV DZ representative of the flow through the left ventricle (another component of the signal DZ).
Figure 7:
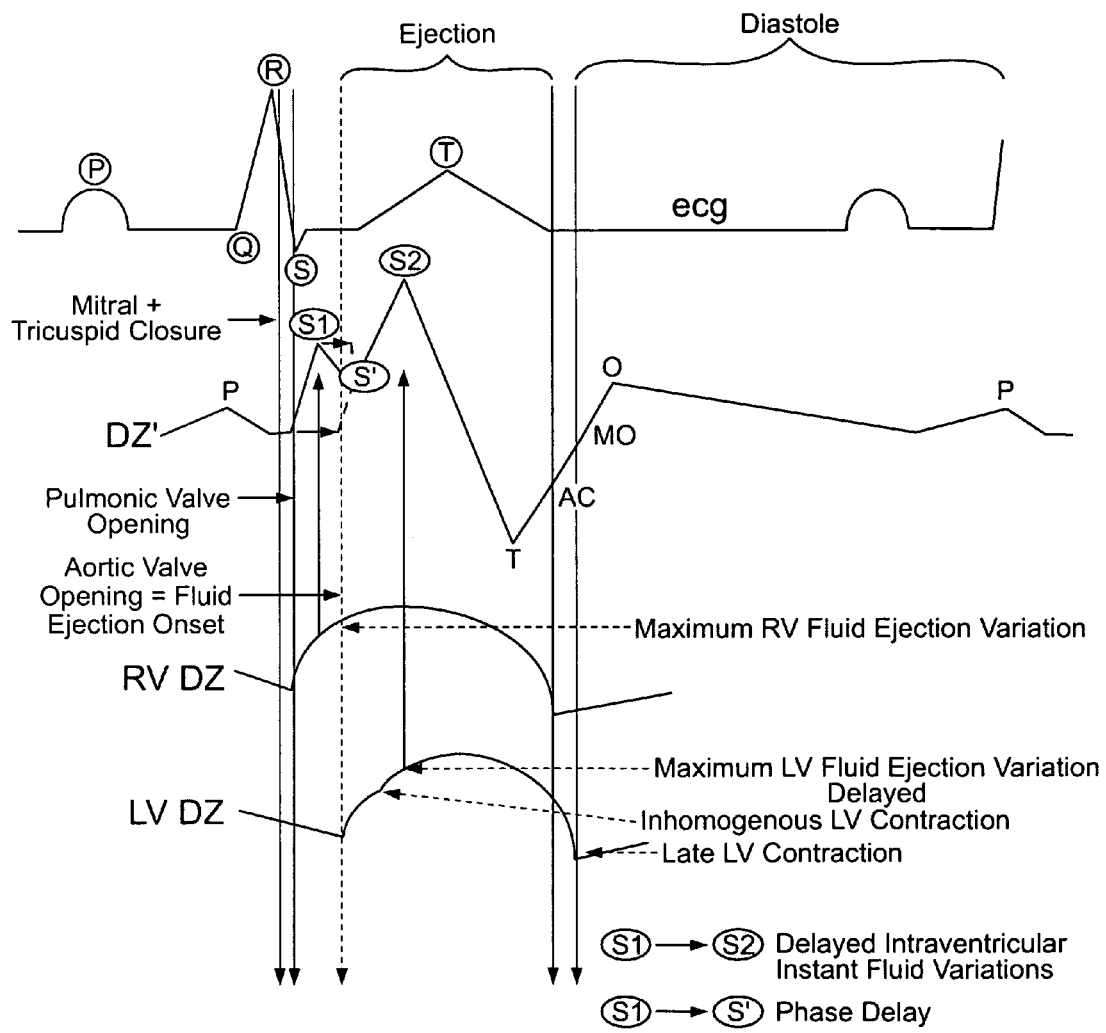
FIG. 7 show an ECG signal similar to that of FIG. 2 (except for a patient with asynchronism), an ICG signal DZ' similar to that of FIG. 2 (except for a patient with asynchronism), a signal RV DZ representative of the flow through the right ventricle (and a component of the signal DZ), and a signal LV DZ representative of the flow through the left ventricle (another component of the signal DZ).

FIGS. 6 and 7 show an ECG signal similar to that of FIG. 2 (except for a patient with asynchronism), an ICG signal DZ' similar to that of FIG. 2 (except for a patient with asynchronism), a signal RV DZ representative of the flow through the right ventricle (and a component of the signal DZ), and a signal LV DZ representative of the flow through the left ventricle (another component of the signal DZ).

As can be seen, the signals RV DZ and LV DZ begin at different times, even greater than that shown in connection with FIG. 4. This results in a double peak at the peak S of the signal DZ'. The first peak S1 typically occurs around the time of maximum fluid ejection variation of the right ventricle and the second peak S2 typically occurs around the time of maximum fluid ejection variation of the left ventricle, as shown. S1 corresponds generally to the maximum variation (acceleration) of the right ventricle blood outflow. S2 corresponds generally to the maximum variation (acceleration) of the aortic flow. Thus, the time between the first peak S1 and the second peak S2 is the interventricular maximum fluid variation delay.

Also, there is a nadir or minimum point S' between peak S1 and peak S2, but not necessarily at the midpoint between peak S1 and peak S2. The time between peak S1 and the point S' is considered the phase delay between the right and left ventricles. The dual peak shape can be seen cycle to cycle on the ICG signal DZ' and seen more pronounced on a cumulative or averaged ICG signal DZ'. The time between peak S1 and point S' can be measured, calculated or determined and represents the phase delay of pulmonic flow onset to aortic flow onset, resulting in an outflow delay due to a later left ventricle electric activation.

Figure 8:
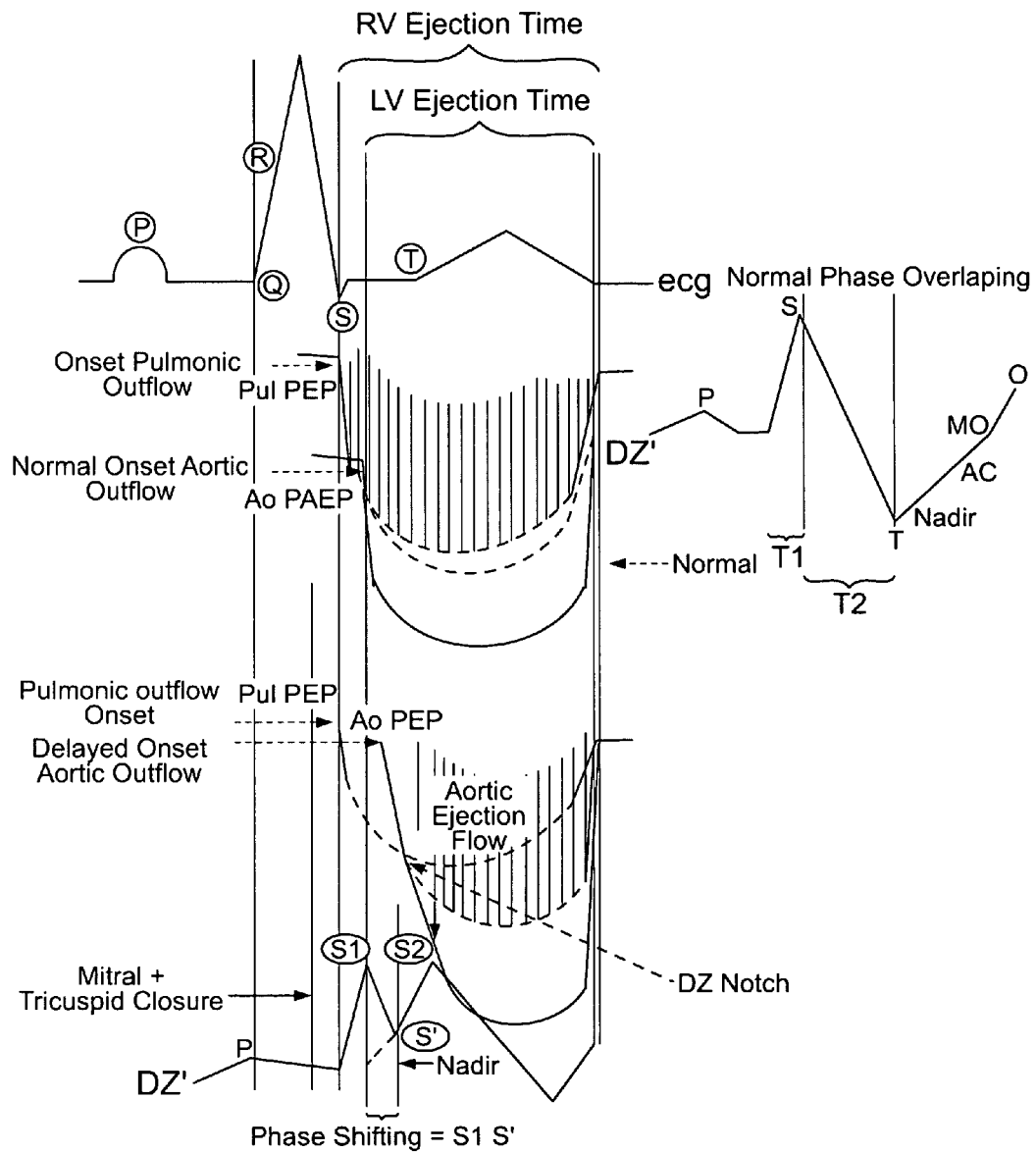
FIG. 8 shows an ECG signal similar to that of FIG. 2, an ICG signal DZ' similar to that of FIG. 2 (normal condition), with corresponding Doppler measurements of pulmonic and aortic outflow, and an ICG signal DZ' similar to that of FIG. 7 (asynchronism condition), with corresponding Doppler measurements of pulmonic and aortic outflow.

FIG. 8 shows an ECG signal similar to that of FIG. 2, an ICG signal DZ' similar to that of FIG. 2 (normal condition), with corresponding Doppler measurements of pulmonic and aortic outflow, and an ICG signal DZ' similar to that of FIG. 7 (asynchronism condition), with corresponding Doppler measurements of pulmonic and aortic outflow. As can be seen, the Doppler measurements can be used to confirm the existence of an asynchronism condition. (Doppler, however, is more difficult to interpret, more expensive to implement, and requires a highly trained operator. Also, because simultaneous recording of right and left ventricular outflow cannot be performed during tissue Doppler method, no asynchronism assessment is possible during arrhythmia—the onset of right or left outflow are related to the length of the previous diastolic phase which changes cycle by cycle.)

Another indicator of interventricular asynchronism is the R wave. A large R wave may indicate asynchronism. In such a case, it is typically a matter of incorrect electric activity through the fibrotic myocardium with a delayed local contraction, e.g., a late left ventricle emptying. This may also result in a bulged signal DZ and consequently a double peaked signal DZ'. In this double peaked signal DZ', S1 typically represents the right ventricle and S2 typically represents the left ventricle. In the case of left bundle branch block, however, the opposite may occur. In the legs over head or upright position, the respective heights of the two peaks S1 and S2 may change according to the pre-load or post-load. Thus, in standing position, for example, the notch or nadir S' may seem more apparent and deeper.

As can be seen in FIG. 8, the pre-ejection time delay appears to be related to the time delay between the two peaks of the DZ' signal. S1 appears to be concomitant with maximum instant pulmonic flow and S2 appears to be concomitant with maximum instant aortic flow.

Figure 9:
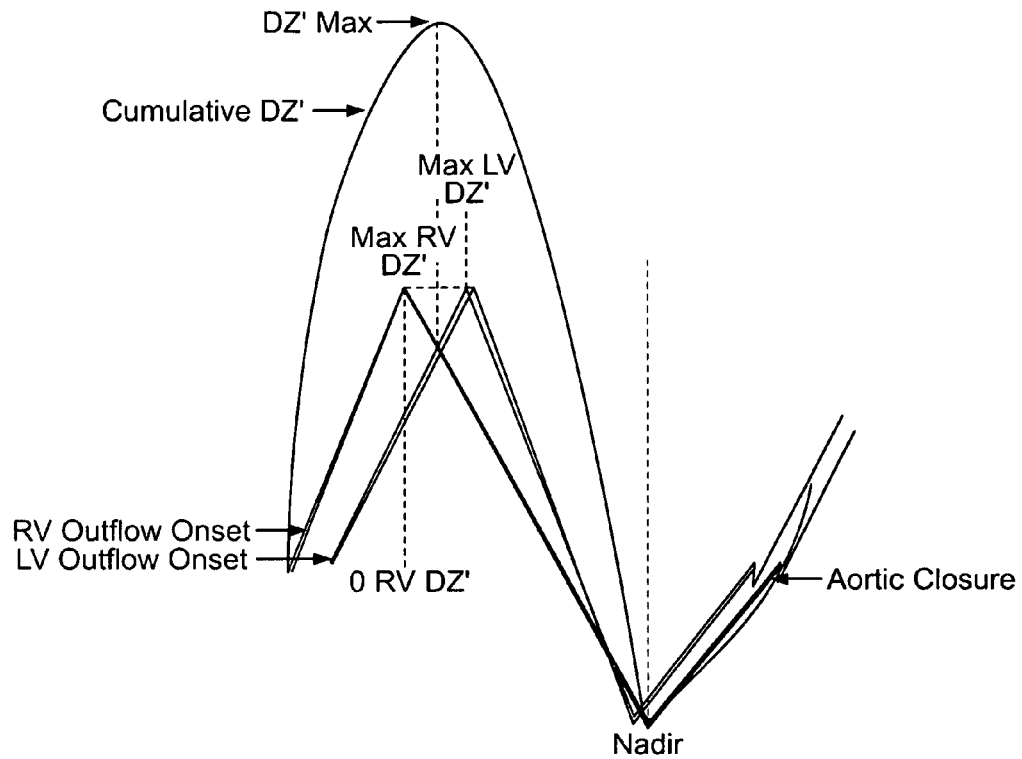
FIG. 9 shows, an ICG signal DZ' (cumulative), a signal RV DZ' representative of the acceleration of the flow through the right ventricle (and a component of the signal DZ'), and the signal LV DZ' representative of the acceleration of the flow through the left ventricle (another component of the signal DZ').

FIG. 9 shows, an ICG signal DZ' (cumulative), a signal RV DZ' representative of the acceleration of the flow through the right ventricle (and a component of the signal DZ'), and the signal LV DZ' representative of the acceleration of the flow through the left ventricle (another component of the signal DZ'). As can be seen, the signal DZ' is dome-shaped without a dual peak, thereby indicating normal cardio function. The individual component signals RV DZ' and LV DZ' do not peak at the same time (max RV DZ' occurs at a different time than max RV DZ'). Nor do the outflows (RV outflow onset and LV outflow onset) occur at the same time. The cumulative signal DZ' does not, however, include a dual peak. The single peak of signal DZ' is located between max RV DZ' and max RV DZ'.

Figure 10:
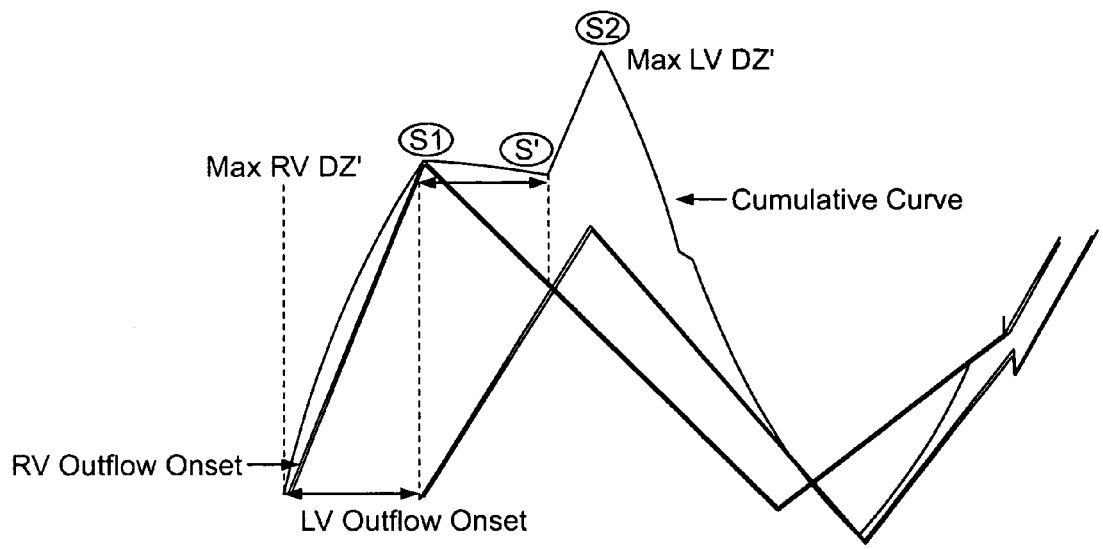
FIG. 10 shows an ICG signal DZ' (cumulative) plotted with the signal RV DZ' representative of the acceleration of the flow through the right ventricle (and a component of the signal DZ'), and the signal LV DZ' representative of the acceleration of the flow through the left ventricle (another component of the signal DZ').

FIG. 10 shows an ICG signal DZ' (cumulative) plotted with the signal RV DZ' representative of the acceleration of the flow through the right ventricle (and a component of the signal DZ'), and the signal LV DZ' representative of the acceleration of the flow through the left ventricle (another component of the signal DZ'). As can be seen, the RV DZ' signal and the LV DZ' signal are generally similar in shape but begin at more significantly different times than as shown in FIG. 9. Because of this greater time difference between RV outflow onset and LV outflow onset (as well as max RV DZ' and max LV DZ') the cumulative signal curve DZ' appears notched (with dual peaks) including first peak S1 (occurring about the time of max RV DZ') and second peak S2 (occurring about the time of max LV DZ'). There is a minimum point S' between peak S1 and peak S2. The time between peak S1 and the minimum point S' may be referred to as the phase delay which is generally representative of the time between right and left mechanical activation.

Multiple conditions may cause the dual peak, with nadir, in the ICG signal DZ'. For example, if a part of the left myocardium has a normal towards mid-ventricle contraction, and if the controlateral segment is not contacting or even dyskinetic, isovolumetric contraction time takes a longer time. Intraventricular blood pressure rises slowly and the opening of the aortic leaflets is delayed with a depressed intra-aortic pressure. This condition may cause the dual peak, with nadir, condition to appear in the ICG signal DZ'. The delayed part of the ventricle, contracting later is pumping towards the controlateral segment which is beginning to relax and therefore is pushed away passively without any active participation of the instant contraction. This lack of coherent contractility explains bad intraventricular pressure and relative short ejection time even if there is a phase delay in the two ventricle activations.

In severe multi-focal desynchronization, the signal DZ' may be multi notched, every notch being related to a flow generated by one specific part of the left ventricular wall mowing. This phenomenon is difficult to correct with a pacemaker.

As can be seen, there is no notch if the aortic outflow onset starts before S1 (dotted vertical line from max RV DZ') because the two mechanical activations merging together. As a result, the cumulative DZ' curve remains smooth. If the LV outflow onset starts after S1, the same onset delay of the two ventricles (which can be assessed with an echocardiogram but not with ICG) occurs at the peak of S with similar time delay (phase delay).

Figure 11:
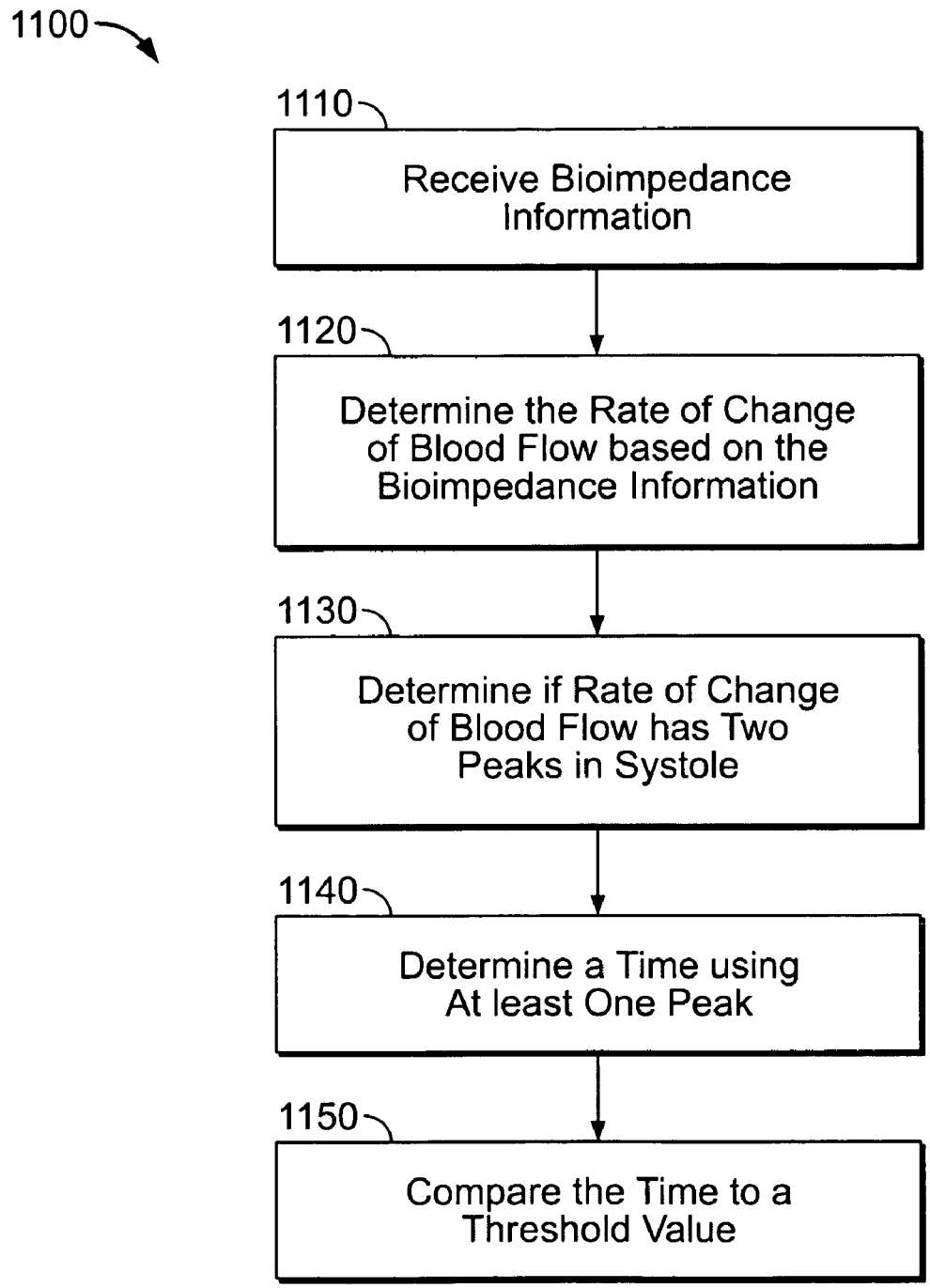
FIG. 11 is a flow diagram of an illustrative method for analyzing cardiographic measurements.

FIG. 11 is a flow diagram of an illustrative method 1100 for analyzing asynchronism which can be performed by an analysis device (e.g., general purpose computer, laptop computer, notebook computer, and the like). As shown in FIG. 11, at 1110, the analysis device receives bioimpedance information of a subject. For example, the analysis device may receive an ICG signal, an ICG Z signal, an ICG DZ signal, an ICG DZ' signal, combinations thereof, and the like. The analysis device may also receive ECG information. The information may be received over a communication link, a serial port, a network communication link, a wireless network, a wireless communication link, combinations thereof, and the like. Thus, the analysis device may be in communication with an ICG device and an ECG device.

At 1120, the analysis device determines the rate of change of blood flow based on the bioimpedance information. If the analysis device received an ICG DZ' signal, then the analysis device may simply use that signal at 1120. Additionally, the analysis device may create (or receive) an averaged ICG DZ' signal that represents an average ICG DZ' signal that has been averaged over multiple cardio cycles. Such an average ICG DZ' signal may be less "noisy" and thus provide a better signal for further analysis. If the analysis device received an ICG DZ signal, then the analysis device may determine the mathematical derivative of that ICG DZ signal to generate the ICG DZ' signal. The ICG DZ signal may first be averaged over multiple cardio cycles before performing the mathematical derivative. Alternatively, the ICG DZ signals may not be averaged before performing the mathematical derivative. In this case, the ICG DZ' signal may be averaged over multiple cardio cycles resulting in an averaged ICG DZ' signal.

At 1130, the analysis device determines if the rate of change of blood flow has two peaks in the systole, as described in connection with FIGS. 5-11. The analysis device may use an ICG DZ' signal or an averaged ICG DZ' signal to determine if the rate of change of blood flow has two peaks in the systole. The analysis device may use peak detection techniques to determine if the rate of change of blood flow has two peaks in the systole.

At 1140, if two peaks were detected at 1130, the analysis device determines a time based on at least one of the two peaks. For example, the analysis device may determine the time of a nadir between the two peaks and then determine the time from the first peak to the nadir. Further, the analysis device may determine the time from the first peak to the second peak, the time from the nadir to the second peak and the like. The analysis device may use an ICG DZ' signal or an averaged ICG DZ' signal in determining the time. The analysis device may automatically determine the time or may rely on manual operator input to determine the time. Typically, the analysis device will automatically determine the time and allow an operator to manually adjust the determined time. For example, the analysis device may automatically determine the time between the first peak and the nadir, graphically display the ICG DZ' signal (or averaged signal), display an indication of time of the first and the nadir on the graphical display (e.g., by displaying vertical lines at the first peak and the nadir), and display the calculated time. Then the analysis device, may receive operator inputs that adjust the time of the first peak, the nadir, or the like (e.g., via a dragging and dropping cursor operation). The analysis device may then recalculate and display a new time based on the operator adjusted time of the first peak, the nadir, or the like.

At 1150, the analysis device compares the determined time to a threshold value which may be predefined, predetermined, or the like. For example, the time may be compared to about 40 milliseconds, 45 milliseconds, 50, milliseconds, 60 milliseconds, and the like. This comparison may determine how a patient is treated as described in more detail below in connection with FIG. 12 (and described above in connection with FIGS. 5-10).

Figure 12:
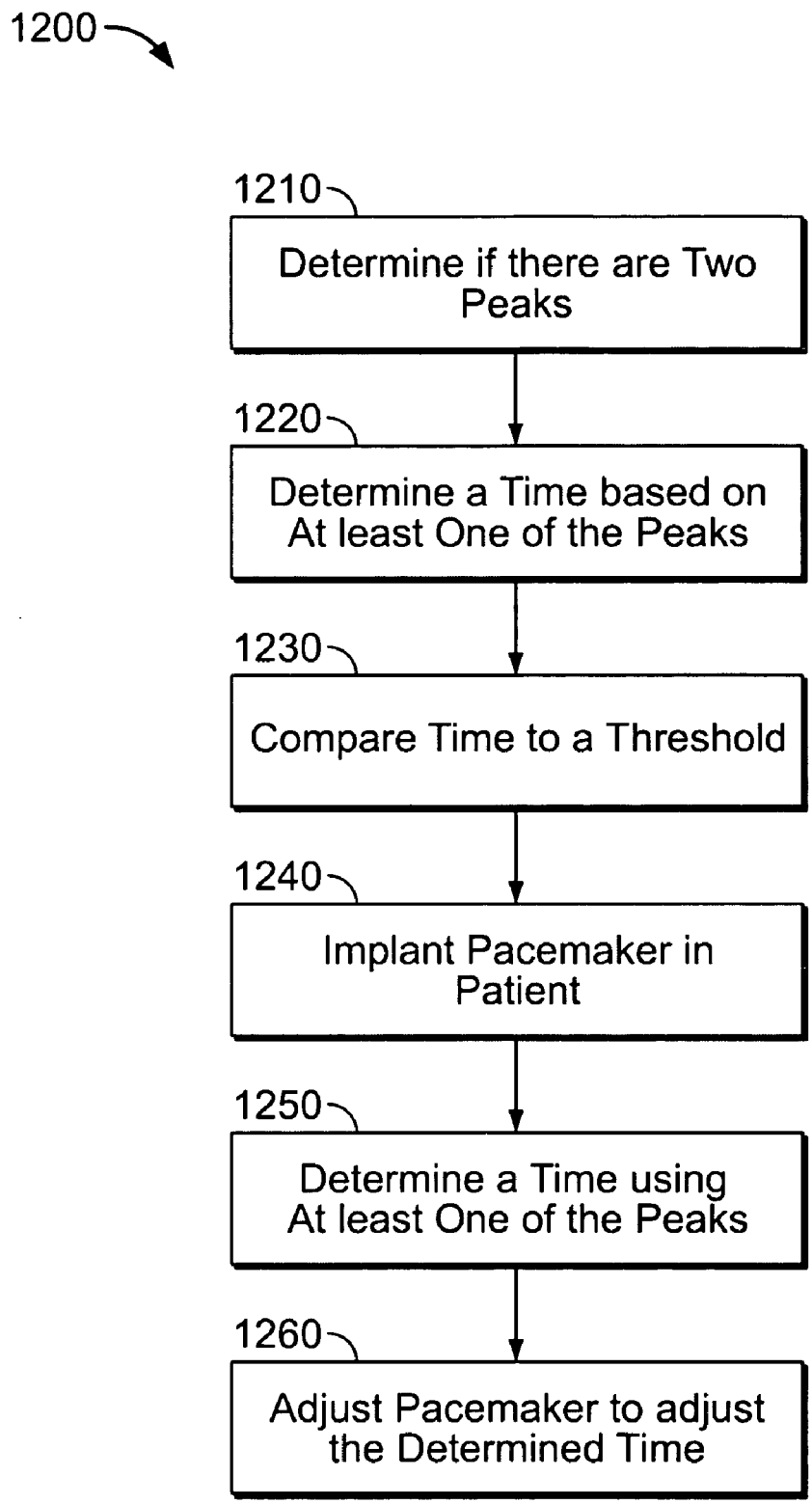
FIG. 12 is a flow diagram of another illustrative method for analyzing and using cardiographic measurements.

FIG. 12 is a flow diagram of an illustrative method 1200 for analyzing and treating interventricular and intraventricular asynchronism. As shown in FIG. 12, at 1210, the analysis device or practitioner determines if the rate of change of blood flow has two peaks in the systole of a subject. The practitioner may use the analysis device in making the determination. If there are not two peaks, the practitioner may not install a pacemaker, as the subject may not have asynchronism. If there are two peaks, the method proceeds to 1220.

At 1220, the analysis device and/or practitioner determine a time based on at least one of the peaks, as described in connection with 1140 of FIG. 11. At 1230, the analysis and/or practitioner compare the time to a threshold, as described in connection with 1150 of FIG. 11.

At 1240, if the determined time is greater than the threshold, then the practitioner or other practitioner implants a pacemaker because the subject likely has asynchronism. If, however, the determined time is less than the threshold, the practitioner or other practitioner does not implant a pacemaker because the subject likely does not have asynchronism.

At 1250, after the implantation of the pacemaker, the analysis device or practitioner determines a new time, for example, using the same technique as described in connection with 1220. If the time is less than a threshold (e.g., about 25, 30, 35, 40 milliseconds), the practitioner or other practitioner may not make any adjustments to the implanted pacemaker.

At 1260, if the new time is greater than a threshold, the practitioner or other practitioner may make adjustments to the implanted pacemaker to decrease the time determined at 1250. 1250 and 1260 may be repeated iteratively until the time determined at 1250 is below the threshold or until a maximum number of adjustments has been made. For example, during implantation of the pacemaker, the practitioner may adjust the locations of the pacemaker probes (e.g., the right atria probe, the right ventricle probe, the left ventricle probe) and then determine if the time has decreased below 25 milliseconds. If the time has not decreased below 25 milliseconds, the practitioner may make another adjustment to the position of the pacemaker probes. Generally, the goal in making adjustments is to adjust the determined time (e.g., the time or phase delay between the first peak S1 and the nadir S) to somewhere between about 20 and 25 millisecond, which is generally considered normal physiologic asynchronism. After implantation of the pacemaker, the practitioner may adjust the stimulation delays (e.g., the AV delay, the DV delay) of the pacemaker probes and then determine if the time has decreased below 25 milliseconds. If the time has not decreased below 25 milliseconds, the practitioner may make another adjustment to the position of the pacemaker probes. Generally, the goal in making adjustments is to adjust the time between the two peaks to somewhere between about 20 and 25 millisecond, which is generally considered normal physiologic asynchronism.

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "information carrier" comprises a "machine-readable medium" that includes any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal, as well as a propagated machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Although a few variations have been described in detail above, other modifications are possible. For example, the logic flow depicted in the accompanying figures and described herein, do not require the particular order shown, or sequential order, to achieve desirable results. Other embodiments may be within the scope of the following claims.

What is claimed is:

1. A computer program product, tangibly embodied on computer-readable media, the computer program product being operable to cause a data processing apparatus to:
   receive bioimpedance information of a subject;
   determine a rate of change of blood flow based on the bioimpedance information;
   determine if the rate of change of blood flow includes at least two peaks during the systole of the subject;
   if the rate of change of blood flow includes at least two peaks, determine a time based on at least one of the two peaks; and
   compare the determined time to a threshold time.

2. The computer program product as in claim 1, wherein receiving bioimpedance information comprises receiving at least one of an impedance cardiography signal, an impedance cardiography signal representative of blood volume, an impedance cardiography signal representative of blood flow, and an impedance cardiography signal representative a rate of change of blood flow.

3. The computer program product as in claim 1, wherein determining the rate of change of blood flow based on the bioimpedance information comprises at least one of receiving an impedance cardiography signal representative of a rate of change of blood flow and receiving an impedance cardiography signal representative of blood flow then taking the mathematical derivative of the impedance cardiography signal representative of blood flow.

4. The computer program product as in claim 1, wherein determining the rate of change of blood flow comprises averaging a rate of change of blood flow over multiple cardio cycles.

5. The computer program product as in claim 1, wherein determining if the rate of change of blood flow includes at least two peaks comprises automatically determining if the rate of change of blood flow includes at least two peaks during the systole of the subject.

6. The computer program product as in claim 1, wherein determining a time based on at least one of the two peaks comprises:
   determining a nadir between the two peaks; and
   determining a time between the first peak and the nadir.

7. The computer program product as in claim 6, wherein determining a time based on at least one of the two peaks comprises automatically determining the time between the first peak and the nadir.

8. The computer program product as in claim 6, wherein determining a time based on at least one of the two peaks comprises:
   automatically determining the time between the first peak and the nadir;
   receiving an input from an input device adjusting a time of at least one of the first peak time and the nadir;
   adjusting the time of at least one of the first peak time and the nadir based on the received input; and
   determining a new time difference between the first peak time and the nadir based on the time adjustment.

9. The computer program product as in claim 1, wherein comparing the determined time to a threshold time comprises comparing the determined time to forty milliseconds.

10. The computer program product as in claim 1, wherein comparing the determined time to a threshold time comprises comparing the determined time to a threshold between twenty-five milliseconds and sixty milliseconds.

11. The computer program product as in claim 1, wherein the computer program product is further operable to cause the data processing apparatus to:
    indicate asynchronism if the determined time is greater than the threshold time.

12. A method for using cardiographic measurements of a subject having a cardio cycle, the cardio cycle comprising a systole, the method comprising:
    determining a rate of change of blood flow;
    determining if the rate of change of blood flow has at least two peaks during the systole of the subject;
    if there are at least two peaks, determining a time difference based on at least one of the two peaks;
    comparing the determining time to a threshold time;
    if the determining time is greater than the threshold time, implanting a pacemaker in the subject; and
    if the determining time is not greater than the threshold time, not implanting a pacemaker in the subject.

13. The method as in claim 12, wherein if the determined time is not greater than the threshold time, not implanting a pacemaker in the subject comprises treating the subject with a conventional heart treatment.

14. The method as in claim 12, wherein determining a rate of change of blood flow comprises determining a rate of change of blood flow with the subject in at least one of a standing position and a legs over head position.

15. The method as in claim 12, wherein determining a time difference based on at least one of the two peaks comprises:

determining a nadir between the two peaks; and determining a time between the first peak and the nadir.

16. The method as in claim 15, wherein the method further comprises:

determining, subsequent to implantation of the pacemaker, a new rate of change of blood flow;

determining, subsequent to implantation of the pacemaker, if the new rate of change of blood flow includes at least two peaks during the systole of the subject;

if the new rate of change of blood flow includes at least two new peaks:

determining a new nadir between the two new peaks;

determining a new time between the new first peak and the new nadir;

if the new determining time is greater than a threshold time, then adjusting the pacemaker; and if the new determining time is not greater than the threshold time, then not adjusting the pacemaker.

17. The method as in claim 16, wherein adjusting the pacemaker comprises adjusting a probe position of the pacemaker during implantation of the pacemaker.

18. The method as in claim 16, wherein adjusting the pacemaker comprises adjusting a stimulation delay of the pacemaker after implantation of the pacemaker.

* * * * *

UNITED STATES PATENT AND TRADEMARK OFFICE
CERTIFICATE OF CORRECTION

| | | |
|---|---|---|
| PATENT NO. | : 7,569,019 B2 | Page 1 of 1 |
| APPLICATION NO. | : 11/454248 | |
| DATED | : August 4, 2009 | |
| INVENTOR(S) | : Frank Bour | |

It is certified that error appears in the above-identified patent and that said Letters Patent is hereby corrected as shown below:

Column 12, line 53, claim 12, delete "determining" and insert -- determined --.

Column 12, line 54, claim 12, delete "determining" and insert -- determined --.

Column 12, line 56, claim 12, delete "determining" and insert -- determined --.

Column 14, line 3, claim 16, delete "determining" and insert -- determined --.

Column 14, line 5, claim 16, delete "determining" and insert -- determined --.

Signed and Sealed this

Thirteenth Day of October, 2009

David J. Kappos
*Director of the United States Patent and Trademark Office*